United States Patent [19]

Aleshin et al.

[11] Patent Number: 5,062,301.

[45] Date of Patent: Nov. 5, 1991

[54] SCANNING DEVICE FOR ULTRASONIC QUALITY CONTROL OF ARTICLES

[76] Inventors: Nikolai P. Aleshin, 15 Parkovaya ulitsa, 18, korpus 1, kv. 109; Vladimir J. Baranov, Schelkovskoe shosse, 58, Korpus 2, kv. 17, both of Moscow; Vyacheslav M. Dolgov, Scherbinka, ulitsa Pushkinskaya, 6, kv. 18, Moskovskaya oblast; Alexandr A. Yarovoi, prospekt Mira, 25, kv. 48, Nikolaev; Oleg A. Preobrazhensky, ulitsa Muranovskaya, 13b, kv. 183, Moscow, all of U.S.S.R.

[21] Appl. No.: 381,395

[22] PCT Filed: Feb. 29, 1988

[86] PCT No.: PCT/SU88/00048

§ 371 Date: Jun. 19, 1989

§ 102(e) Date: Jun. 19, 1989

[87] PCT Pub. No.: WO89/05451

PCT Pub. Date: Jun. 15, 1989

[30] Foreign Application Priority Data

Dec. 10, 1987 [SU] U.S.S.R. .............................. 4336106

[51] Int. Cl.[5] ...................... G01N 29/24; G01N 29/26
[52] U.S. Cl. ........................................ 73/629; 73/635; 73/620; 73/641
[58] Field of Search ................ 73/629, 618, 620, 641, 73/633, 635

[56] References Cited

U.S. PATENT DOCUMENTS

| 3,504,534 | 4/1970 | Mandula | 73/638 |
| 4,010,636 | 3/1977 | Clark et al. | 73/637 |

FOREIGN PATENT DOCUMENTS

| 743287 | 12/1968 | Belgium | 73/641 |
| 555333 | 5/1977 | U.S.S.R. . | |
| 1128161 | 12/1984 | U.S.S.R. . | |
| 1173304 | 8/1985 | U.S.S.R. | 73/620 |
| 1174851 | 8/1985 | U.S.S.R. | 73/620 |
| 1320740 | 6/1987 | U.S.S.R. | 73/635 |
| 1343989 | 1/1974 | United Kingdom . | |
| 1415389 | 11/1975 | United Kingdom . | |

Primary Examiner—Michael J. Tokar
Assistant Examiner—Rose M. Finley
Attorney, Agent, or Firm—Ladas & Parry

[57] ABSTRACT

The scanning device for ultrasonic control of articles comprises a suspension assembly (7) for mounting ultrasonic transducers on a motion mechanism (6) of the scanning device. The assembly (7), in its turn, includes flexible members (8) positioned above a surface (4) of an article (2) under inspection, having ultrasonic transducers (1) fixedly mounted thereon and contained within a housing (3), a beam (9) extending above the flexible members (8) and mechanically connected therewith, two self-aligning supports (10), each including two parts, that is, an arcuate member (16) and rollers (17) so arranged with respect to each other that their relative displacement takes place about a rolling axis (15) common to both supports (10), extending along the surface (4) of the article (2), and two rockers (11) operatively connected to the beam (9) and to the motion mechanism (6).

12 Claims, 11 Drawing Sheets

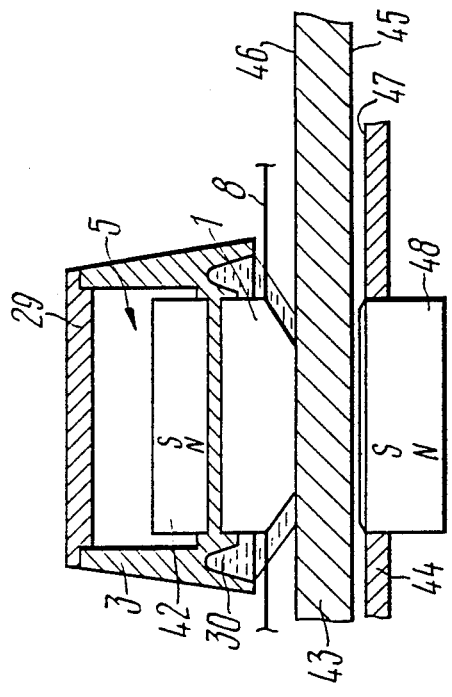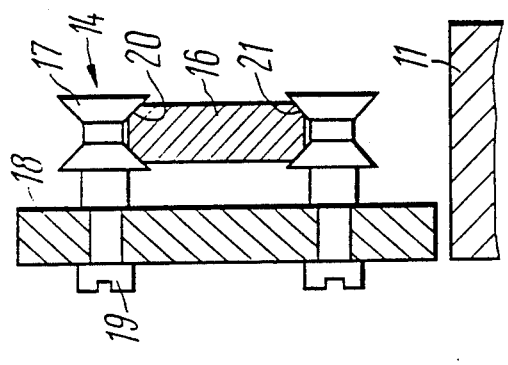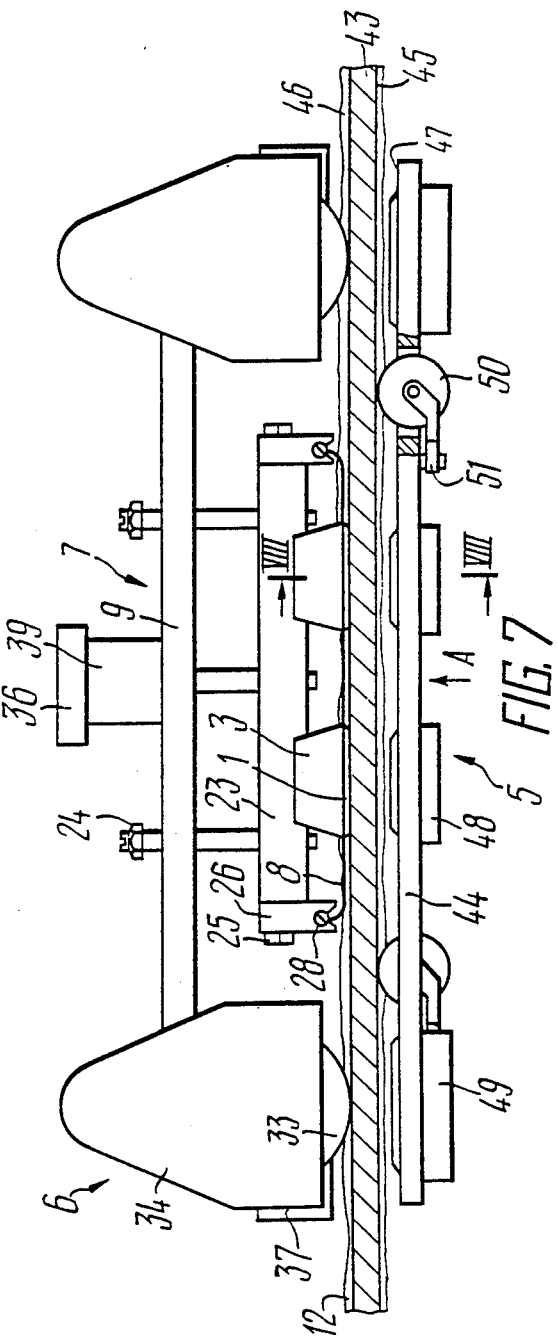

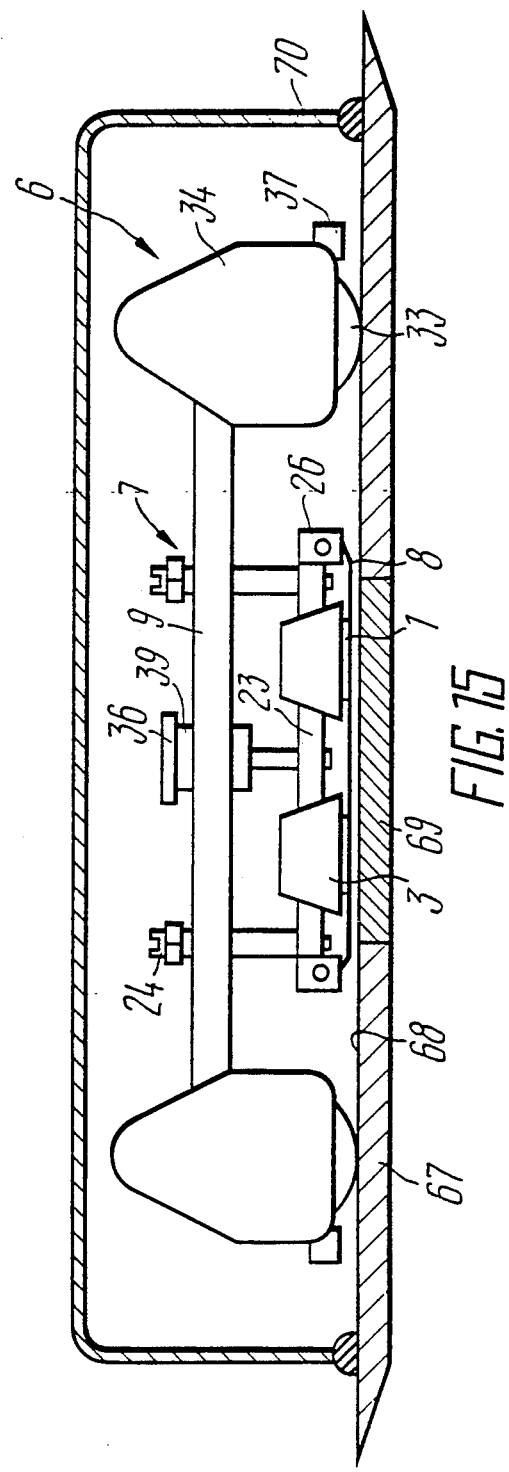

SCANNING DEVICE FOR ULTRASONIC QUALITY CONTROL OF ARTICLES

TECHNICAL FIELD

The present invention relates to apparatus for nondestructive inspection and quality control of articles, and more particularly it relates to scanning device for ultrasonic quality control of articles.

BACKGROUND ART

There is known an apparatus for ultrasonic quality control of articles, comprising ultrasonic transducers mounted by means of a suspension assembly on a carriage with supporting rollers engaging the surface of the article being inspected (SU, A, 555333).

This device would not ensure stable positioning of the ultrasonic transducers with respect to the surface of the article under inspection, as it is devoid of operative links supporting reliable orientation of the ultrasonic transducers, as they are moved over the surface of the article. The rigid mounting of the suspension assembly with the ultrasonic transducers on the carriage would not enable them to navigate such obstacles as the beads of welds, metal splashes left by the welding operation, and the like—as in such cases a toppling torque may be produced, resulting in a breakdown of the suspension assembly of the device.

Moreover, the operation of this device is characterized by inadequate reliability and credibility of quality control of articles with either planar or curvilinear surfaces in different spatial attitudes of the device.

There is further known a scanning device for ultrasonic quality control of articles, comprising ultrasonic transducers set on the article being inspected and urged against its surface by a hold-down assembly, the transducers being mounted on a motion mechanism by means of a suspension assembly (SU, A, 1128161).

In this scanning device the suspension assembly of the ultrasonic transducers on the motion mechanism includes carriages articulated on pantographs fast with the motion mechanism.

The articulated parallelogram of each pantograph is biased by a spring and serves as the suspension assembly of the respective ultrasonic transducers.

However, this design of the suspension assembly is structurally complicated and results in relatively great dimensions and weight, which hinders the operation of quality control of articles with planar and curvilinear surfaces in different spatial attitudes of the scanning device, impairing the reliability and credibility of quality control of articles made of diverse materials, either ferromagnetic or non-ferromagnetic.

Furthermore, this design of the device would not provide for overcoming such obstacles as metal splashes left after the welding or the beads of welds, because the moment a carriage with the ultrasonic transducers rolls onto an obstacle, there is produced a toppling torque owing to the axes of the pivots joining the carriages to the pantographs being situated relatively high above the surface of the article under inspection.

DISCLOSURE OF THE INVENTION

This invention is to provide a scanning device for ultrasonic quality control of articles, wherein the structure of the suspension assembly of ultrasonic transducers is simple and adapted for reliable ultrasonic inspection of a broad range of articles with either planar or curvilinear surfaces, made of either ferromagnetic or non-ferromagnetic materials, in different spatial attitudes of the scanning device, while being small and not heavy.

These and other objects are attained in a scanning device for ultrasonic quality control of articles, comprising ultrasonic transducers adapted to contact the article under inspection and to be urged against the surface thereof by hold-down means, mounted on the motion mechanism of the scanning device by means of a suspension assembly, in which device, in accordance with the invention, the suspension assembly of the ultrasonic transducers on the motion mechanism of the scanning device includes flexible members positionable above the surface of the article under inspection along the direction of the travel of the device, preset with the motion mechanism, having the ultrasonic transducers fixedly mounted thereon, a beam extending above the flexible members along the direction of the travel of the device, mechanically connected with the flexible members, at least two self-aligning supports of which one part is carried by the beam and the other part is arranged with respect to the first-mentioned part in such a way that relative displacement of the two parts takes place relative to a rolling axis common to the self-aligning supports, situated in close proximity to the surface of the article under inspection, and two rockers operatively connected with the beam and with the motion mechanism.

It is expedient that one part of each self-aligning supports should be in the form of an arcuate member of which the longitudinal central axis is the common rolling axis for both self-aligning supports, mounted on one end of the beam, the other part including at least three rollers carried by a common base, engaging the working surfaces of the arcuate member and operatively connecting one of the rockers with the beam through the arcuate member and the base.

It is reasonable that one part of each self-aligning supports should include a guideway fast with the beam, having two cylindrical working surfaces and one planar working surface interconnecting them, the other part including a shell mechanically joined to the flexible members, having two cylindrical working surfaces interconnected by one planar surface, the last-mentioned cylindrical working surfaces being congruent with the respective first-mentioned cylindrical working surfaces and in engagement therewith, the longitudinal axes of all said cylindrical working surfaces coinciding and being the common rolling axis for both self-aligning supports.

For quality control of articles of ferromagnetic materials, it is expedient that the hold-down means urging the ultrasonic transducers against the surface of the article under inspection should include main permanent magnets directly overlying the respective ultrasonic transducers fixedly mounted on the flexible members.

For quality control of articles of non-ferromagnetic materials, it is reasonable that the hold-down means urging the ultrasonic transducers against the surface of the article under inspection should include a platform situated adjacent to the surface of the article under inspection at the side thereof, opposite to the side at which the inspection is performed, the platform being adapted to automatically follow the path of the travel of the scanning device, the platform having additional permanent magnets mounted thereon with their poles facing the poles of opposite polarity of the respective main permanent magnets, symmetrically therewith.

The disclosed structure of a scanning device for ultrasonic quality control of articles provides for enhanced reliability and credibility of the quality control operation, while allowing to reduce the dimensions and weight of the scanning device, as a whole, and to substantially simplify its design.

Furthermore, the disclosed device provides for broadening the range of inspected articles with either planar or curvilinear surfaces, made of either ferromagnetic or non-ferromagnetic materials, while performing the quality control operation in different spatial attitudes of the device.

The fixed mounting of the ultrasonic transducers on the flexible members provides for overcoming obstacles on the surface of the article under inspection, such as splashes of metal left by the welding operation or the beads of welds, irrespective of the curvature of the surface of the article.

The small dimensions and weight of the disclosed scanning device enable one operator to handle it.

The permanent magnets of the hold-down means of the disclosed device provide for using a ferromagnetic fluid for maintaining stable acoustic contact between the surface of the article under inspection and the ultrasonic transducers.

BRIEF DESCRIPTION OF DRAWINGS

These and other objects and advantages of the present invention will be made apparent in the following description of its embodiments, with reference being made to the accompanying drawings, wherein:

FIG. 6 shows on an enlarged scale a sectional view taken on line VI—VI of FIG. 5;

FIG. 7 is a partly broken away side view of another embodiment of a scanning device in accordance with the invention, with the inspected article shown in section;

FIG. 8 shows an enlarged sectional view taken on line VIII—VIII of FIG. 7;

FIG. 15 shows, on a smaller scale, a side view of the scanning device of FIG. 1, mounted on a pallet with a test specimen, shown in section.

BEST MODE FOR CARRYING OUT THE INVENTION

Figure 1:
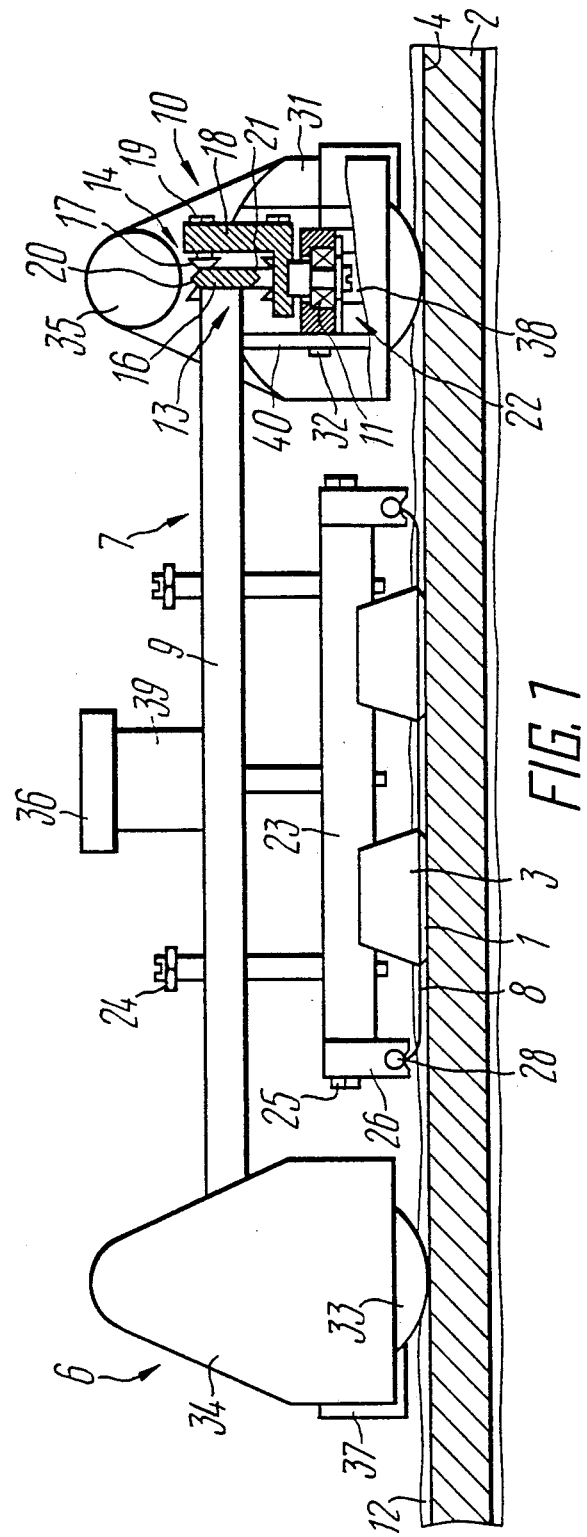
FIG. 1 is a partly broken away sectional side view of a scanning device for ultrasonic quality control of articles, mounted on an article under inspection according to the invention.

In the drawings, the scanning device for ultrasonic quality control of articles, embodying the invention, comprises ultrasonic transducers 1 (FIG. 1) adapted to contact the article 2 under inspection. In the embodiment being described, the ultrasonic transducers 1 are enclosed within their respective housings 3 (FIGS. 1 to 3).

Figure 3:
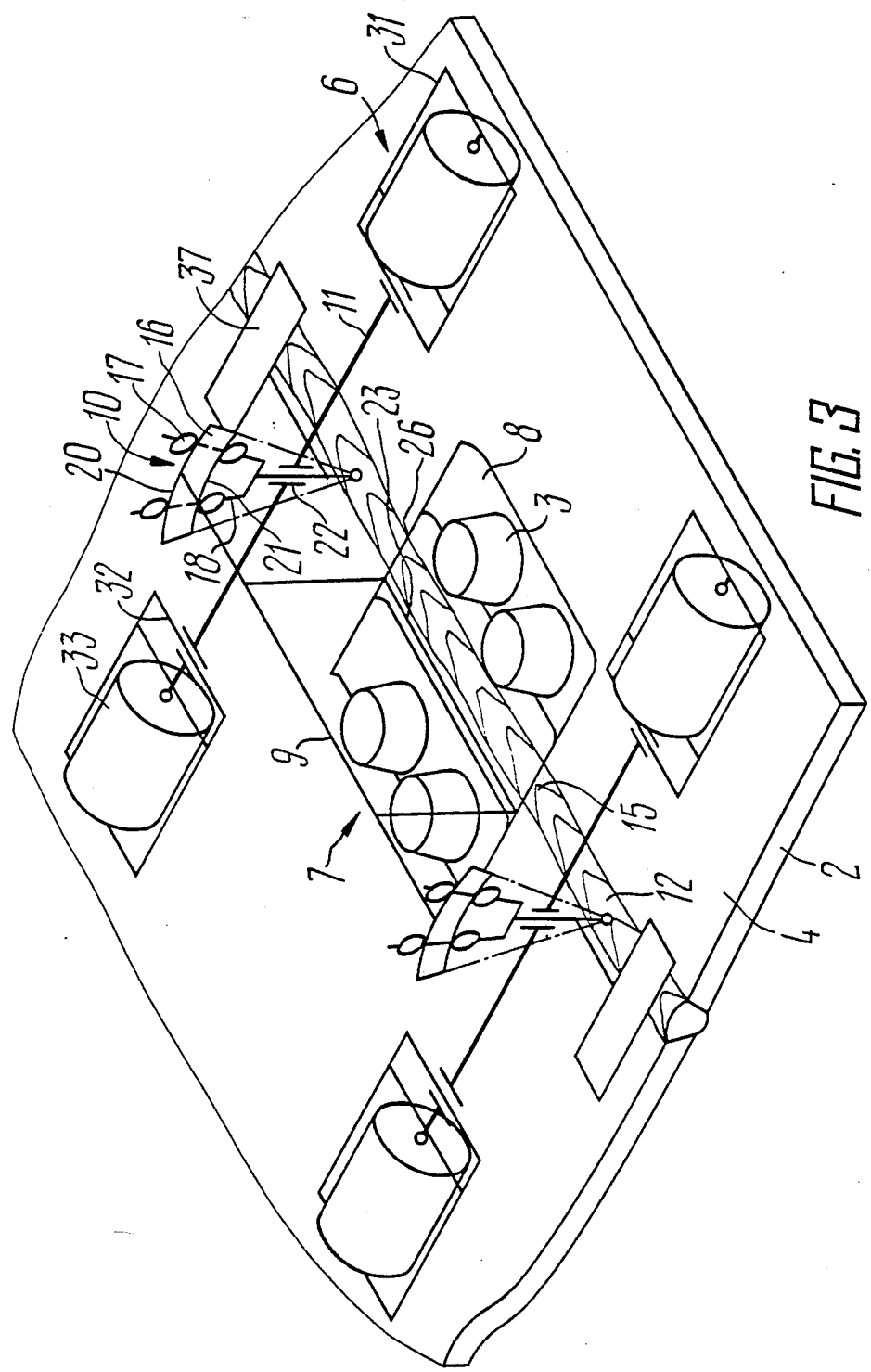
FIG. 3 is a mechanical diagram of the device of FIG. 1.
Figure 4:
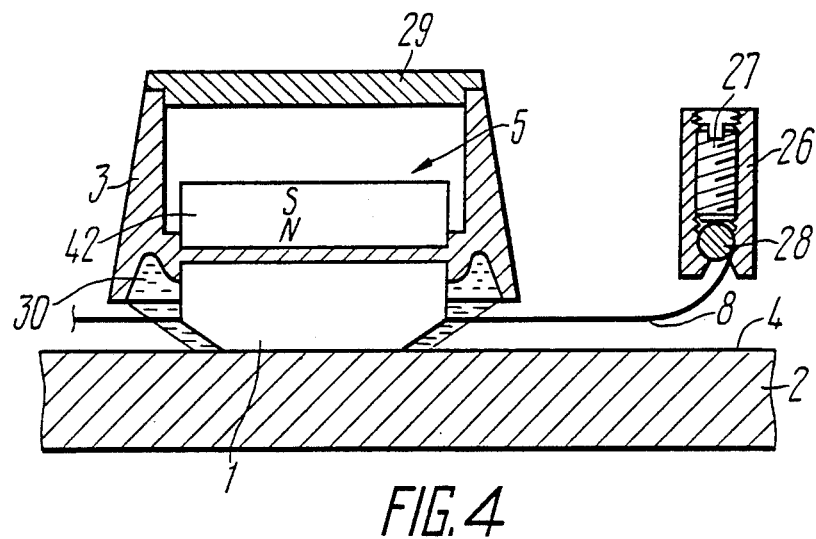
FIG. 4 shows on an enlarged scale a sectional view taken on line IV—IV of FIG. 2.

The ultrasonic transducers 1 (FIG. 4) are urged against the surface 4 of the article 2 by hold-down means 5, and are mounted on a motion mechanism 6 (FIGS. 1 to 3) by means of a suspension assembly 7.

The suspension assembly 7 includes flexible members 8, a beam 9, two self-aligning supports 10, and two rockers 11.

Figure 2:
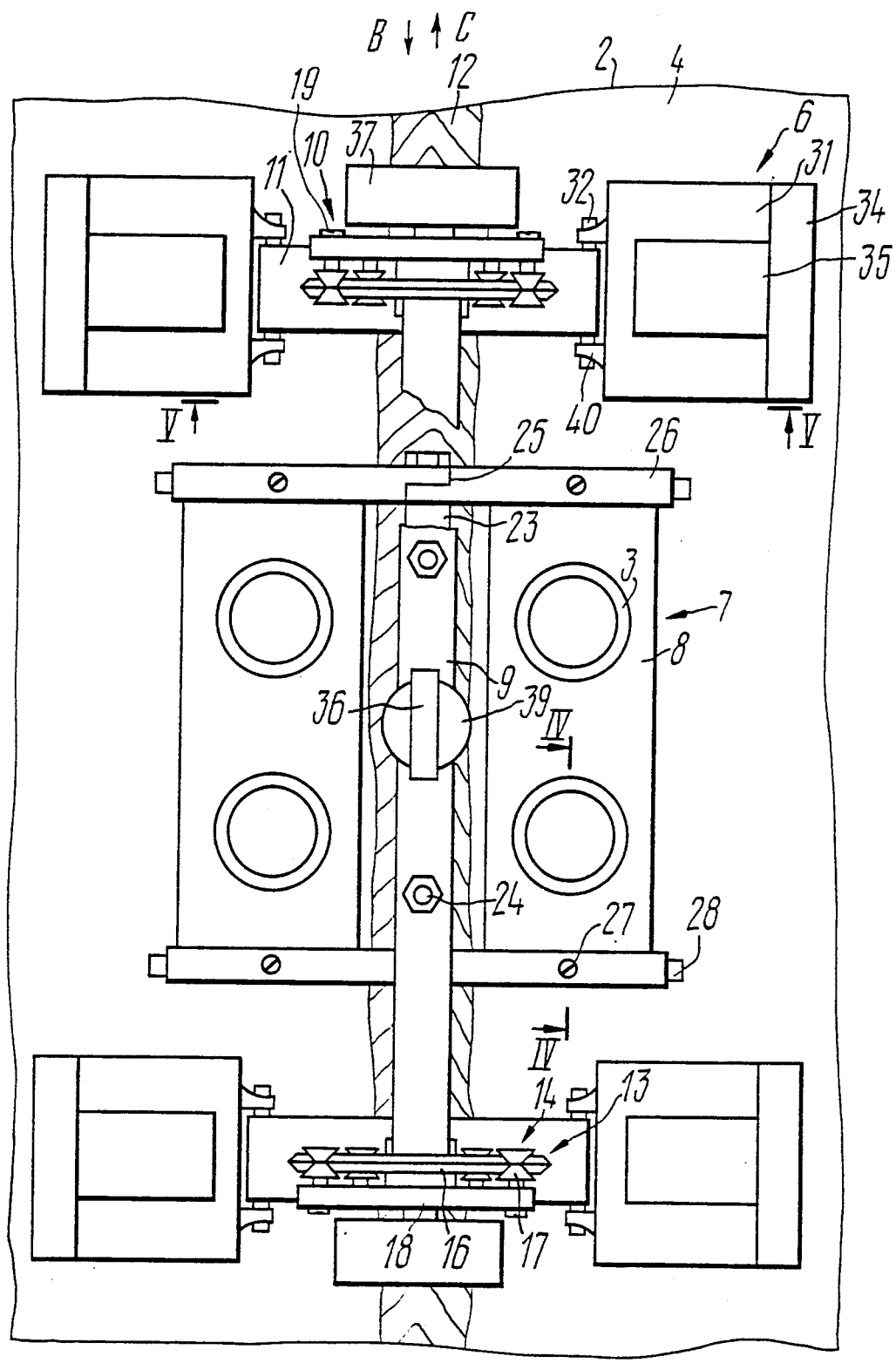
FIG. 2 is a partly broken away view in plan of the device of FIG. 1.

The flexible members 8 which in the presently described embodiment are in the form of metal bands, are positioned directly above the surface 4 of the article 2 under inspection, longitudinally of the direction of the travel of the device, preset with the motion mechanism 6, the direction being indicated with arrows B and C in FIG. 2, to follow a weld 12 of the article 2. The two flexible members 8 of the presently described embodiment are arranged to both sides of the weld 12. The flexible members 8 (FIGS. 1 and 4) have the ultrasonic transducers 1 secured thereon.

Overlying the flexible members 8 (FIG. 2) along the direction of the travel of the device embodying the invention is the beam 9 mechanically connected with the flexible members 8.

Figure 5:
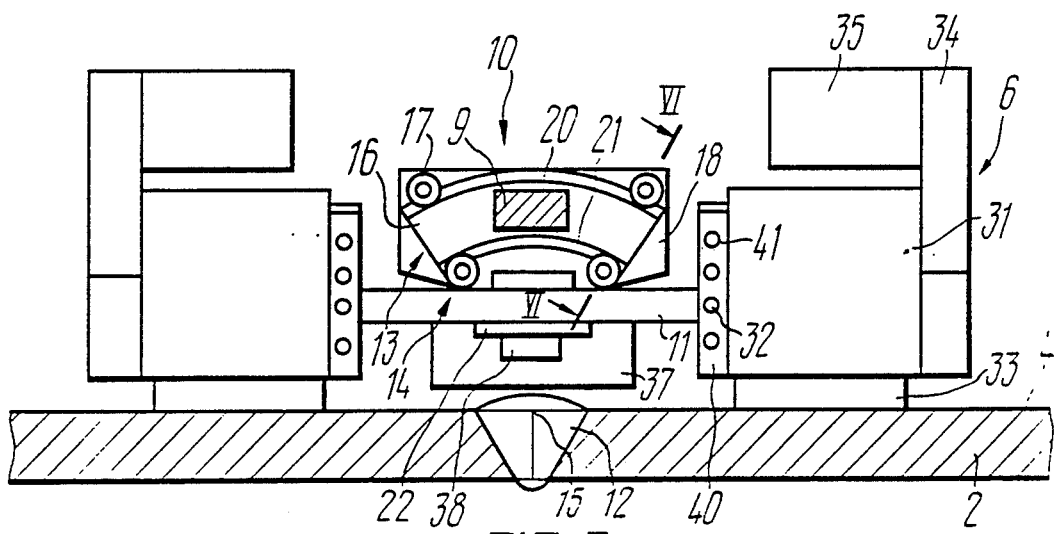
FIG. 5 is a sectional view taken on line V—V of FIG. 2.

The self-aligning supports 10 (FIG. 5) have each one its part 13 carried by the beam 9 and the other part 14 arranged with respect to the first part 13 so that relative displacement of the two parts 13 and 14 takes place about a rolling axis 15 common to both self-aligning supports 10, the rolling axis 15 directly adjoining the surface 4 of the article 2 under inspection. In the embodiment being described, this imaginary rolling axis 15 belongs directly to the surface 4 of the article 2, and the device includes only two self-aligning supports 10.

However, a device embodying the invention may have three or even more self-aligning supports, depending on the number of the ultrasonic transducers it carries.

The rockers 11 (FIGS. 1 and 2) are operatively connected with the beam 9 and with the motion mechanism 6.

In the embodiment of the scanning device being described, one part 13 (FIG. 5) of each self-aligning support 10 is in the form of a partly annular arcuate member 16 of which the imaginary central longitudinal axis 15 is the common axis of rolling of both self-aligning supports 10, mounted on one end of the beam 9, which can be clearly seen in FIG. 2.

The other part 14 (FIG. 6) of each self-aligning support 10 includes four rollers 17 mounted on their common base 18 with the aid of screws 19, engaging the working surfaces 20 (FIGS. 3 and 5) and 21 of the respective arcuate member 16, for establishing operative connection of the beam 9 with the respective rocker 11 through the arcuate member 16, the base 18 and a pivot 22.

However, the number of the rollers can also be either three, or more than four, depending on the actual values of the loads to be taken up by the rollers as the device moves over the surface of the article under inspection.

The mechanical connection of the beam 9 (FIGS. 1 to 3) with the flexible members 8 is effected through a bar 23 mounted on the beam 9 by means of two screw-and-nut couples 24 (FIGS. 1 and 2) arranged adjacent to the ends of the beam 9. The holders 26 of the flexible members 8 are mounted on the opposite ends of the bar 23 by means of respective pivots 25, with the ends of the flexible members 8 secured in the respective holders 26 (FIG. 4) by means of a lock screw 27 and an element 28 for tensioning the respective flexible member 8.

Each housing 3 of the respective ultrasonic transducer 1 has a sealing lid 29 defining jointly with the housing 3 an internal cavity 30 for holding a supply of a ferromagnetic fluid which is preferably employed for maintaining stable acoustic contact between the ultrasonic transducer 1 and the surface 4 of the article 2 under inspection.

The motion mechanism 6 (FIG. 2) of the scanning device being described comprises four housings 31 pivotally joined to the respective ends of the rockers 11 through pivots 32. Each housing 31 (FIG. 1) accommodates therein a magnetic wheel 33 fixed on the output shaft of a reduction gear 34 fast with the housing 31. The drive electric motor 35 (FIG. 2) is mounted on each respective reduction gear 34, the output shaft of the electric motor 35 being in engagement with the input shaft of the reduction gear 34.

However, a scanning device embodying the invention may have a motion mechanism with only two electric motors and reduction gears operatively connected with the wheels carried by the leading rockers in the direction of the intended travel of the device. The actual arrangement depends on the intended spatial attitude of the device in its travel over the surface of the inspected article, e.g. for performing quality control of vertical welds.

The scanning device embodying the invention further comprises a control operation beginning/terminating transmitter 36 (FIGS. 1 and 2) mounted on the beam 9 for sending out signals monitoring the beginning and terminating of a quality control operation, sensors 37 for tracing a weld 12, mounted on the respective bases 18 for generating signals proportional to a deviation of the device from the weld 12 in its travel, angular position sensors 38 (FIG. 5) mounted on the pivots 22 for monitoring the angular positions of the respective rockers 11 relative to the bases 18, and a distance sensor (not shown in the drawings, as unrelated to the essence of the present invention) of the path travelled by the device.

The beam 9 (FIG. 2) further carries a flaw marker 39 operable to apply onto the surface of the article 2 corresponding marks, e.g. ink marks, locating the positions of the flaws in the inspected article 2, detected by the ultrasonic transducers 1 in the travel of the device.

The housings 31 (FIG. 5) have mounted thereon lugs 40 with holes 41 for adjusting the suspension assembly 7 prior to a quality control operation.

When the scanning device embodying the invention is operated for quality control of articles 2 (FIG. 4) of ferromagnetic materials, e.g. of steel, the hold-down means 5 for urging the ultrasonic transducers 1 against the surface 4 of the article 2 under inspection includes permanent magnets (with S and N poles) overlying the respective transducers 1 fixed on their supporting flexible members 8.

When the scanning device embodying the invention is intended for quality control of articles 43 (FIG. 7) of non-ferromagnetic materials, e.g. of aluminium, the basic design of the scanning device is identical with that described hereinabove and illustrated in the appended drawings, FIGS. 1 to 6.

The difference is that the hold-down means 5 (FIGS. 7 and 8) additionally comprises a platform 44 adjoining the surface 45 of the article 43 at the side opposite to the side 46 thereof, at which the control operation takes place. The platform 44 is made so that the curvature of its surface 47 copies the surface 45 of the article 43, the platform 44 being adapted to automatically follow the path of the travel of the scanning device embodying the invention. The hold-down means further includes for this purpose additional permanent magnets 48 (with S and N poles), arranged on the platform 44 for their respective poles S (FIG. 8) to face the poles N of opposite polarity of the main permanent magnets 42, symmetrically with the latter.

The automatic following by the platform 44 of the path travelled by the scanning device embodying the invention is provided for by the magnetic connection established between the wheels 33 (FIG. 7) of the motion mechanism 6 and the main permanent magnets 42, respectively, and the additional permanent magnets 49 and 48 mounted on the platform 44, which provides for reliable engagement of the wheels 33 with the surface 46 of the article 43 being inspected, and for urging the ultrasonic transducer 1 against this surface 46. For this purpose the platform 44 is additionally provided with self-aligning wheels 50 (FIG. 9) mounted on the platform 44 by means of spring-biased hinges 51 for engagement with the surface 45 of the article 43. The spring bias of the hinges 51 make them adjustable for varying the clearance between the surface 45 of the inspected article 43 and the adjoining surfaces of the additional magnets 48 and 49, which is essential for the platform 44 with its magnets 48, 49 and self-aligning wheels 50 to be capable of overcoming eventual obstacles, e.g. the beads of welds.

Illustrated in FIGS. 10 to 14 of the appended drawings is an embodiment of the scanning device in accordance with the invention, which is basically similar to the device illustrated in FIGS. 1 to 6.

The difference resides in a modified design of the self-aligning supports 10 (FIGS. 10 to 13). Thus, one part 13 (FIGS. 10 and 13) of each support 10 is in the form of a guideway 52 with two cylindrical working surfaces 53 and 54, interconnected by a planar working surface 55. The guideway 52 (FIG. 10) is secured to the beam 9 by means of a screw-and-nut couple 24.

The other part 14 of each support 10 is in the form of a shell 56 (FIGS. 10, 12 and 13) mechanically connected with the flexible members 8, having two cylindrical working surfaces 57 (FIG. 10) and 58, interconnected by a planar working surface 59, congruent with the respective cylindrical working surfaces 53 and 54 in engagement therewith. The respective longitudinal central axes of all the cylindrical working surfaces 53 (FIG. 12), 54, 57 and 59 coincide and define the common imaginary rolling axis 15 for both self-aligning supports 10.

However, the device illustrated in FIGS. 10 to 14 may have more than two self-aligning supports 10, depending on the number of the ultrasonic transducers 1.

The mechanical connection of the shell 56 (FIGS. 10 and 13) with the flexible elements 8 is effected by the shell 56 being secured by screws 60 on the bar 23.

The operative connection of the beam 9 (FIG. 12) with the rockers 11 is effected through pivots 22 and 61.

In this embodiment of the disclosed device, the beam 9 is provided with pivots 62 (FIGS. 10 and 11) for broadening the range of surfaces 4 to be inspected and for simplifying the adjustment of the device prior to a quality control operation.

The sensors 37 tracing a weld 12 are mounted on their respective leaf springs 63 with pivots 64, the springs 63 being mounted on the bar 23 through respective pivots 25. The sensors 37 for tracing the weld 12 carry limit switches 65 for deactivating the sensors 37 for periods required for their riding over encountered obstacles, e.g. transverse welds, so as to avoid interference with the true readings of these sensors 37 is tracing the weld 12 being inspected. One of the end switches 65 preferably performs an additional function of interrupting the travel of the whole scanning device when the geometric irregularities of the article 2 under inspection (e.g. the height of the bead of a weld) exceed the tolerable values prescribed by appropriate specifications concerning the article 2 and its welds 12.

The last-described embodiment of the disclosed scanning device is preferred when the device is intended for travel over vertical and inclined surfaces 4 of articles 2, in any direction of the travel.

The housing 3 of the embodiment being described, and of other embodiments as well, carry ferromagnetic screens 66 (FIG. 14) for minimizing the interference of the magnetic leakage fields generated by the respective permanent magnets 42.

For storing a device constructed in accordance with the invention and for preparing it to operation, there is preferably used a pallet 67 (FIG. 15) having its device-supporting surface 68 flush with the surface of a test specimen 69, the pallet being provided with a protective casing 70.

The principle of operation of a scanning device for ultrasonic control of articles, constructed in accordance with the invention, is as follows.

Prior to being operated for quality control of an article 2 (FIG. 1) of a ferromagnetic material, the device embodying the invention, illustrated in FIGS. 1 to 6, is set on the supporting surface 68 (FIG. 15) of the pallet 67 with the test specimen 69. The curvature of the surface 68, the thickness and material of the test specimen 69 should be identical to those of the article 2 to be inspected. The beam 9 is indexed along the intended direction of the travel of the device, indicated with arrows B (FIG. 2) and C. The pivots 32 (FIG. 5) are used to secure the ends of the rockers 11 in the lugs 40 with the holes 41 of the respective housings 31 of the motion mechanism 6, at a height predetermined for the given article 2. The screw-and-nut couples 24 (FIG. 1) are operated to secure the bar 23 on the beam 9 at a spacing from the surface 68 (FIG. 15), sufficient for the bar 23 with the holders 26 mounted thereon by means of the pivots 23 to move unobstructedly over the surface of the bead of a weld 12 (FIG. 1) and over the surface 4 of the article 2. The elements 28 (FIG. 4) are operated to adjust the tension of the flexible members 8, so as to position the ultrasonic transducers 1 properly with respect to the test specimen 69 (FIG. 15), for the ultrasonic transducers 1 to sound out the entire inspected section of the article 2 (FIG. 1), i.e. the entire volume of the weld 12 and of the zones directly adjoining it, and then the lock screws 27 are operated to secure the respective ends of the flexible members 8 jointly with the tensioning elements 28.

A ferromagnetic fluid is poured into the internal cavities 30 (FIG. 4) of the housing 3 to provide for stable acoustic contact between the ultrasonic transducers 1 and the surface 68 (FIG. 15) of the test specimen 69, and the operability of all the ultrasonic transducers 1 is appropriately checked.

The pallet 67 with the inspection-ready device illustrated in FIGS. 1 to 6 is brought against the article 2 to be inspected, in the proper attitude for the travel (along the weld 12), and the disclosed device rolls onto the surface 4 of the article 2 under inspection.

The motion of the scanning device over the surface 4 of the article 2 is effected by rotation of the magnetic wheels 33 (FIGS. 1,5) held in dependable engagement with the surface 4.

When the device illustrated in FIGS. 1 to 6 is operated for inspecting a weld 12, the speed of rotation of the wheels 33 is controlled by signals coming from the sensors 37 for tracing the weld 12, and from the angular position sensors 38.

When one of the leading (in the direction of the travel) wheels 33 encounters an obstacle, e.g. a transverse weld, the leading (in the direction of the travel) rocker 11 rocks relative to the surface 4, the common base 18 with the rollers 17 also rocks, as the rocker 11 and the common base 18 are interconnected by the pivot 22, but the arcuate member 16 of the leading self-aligning support turns among the rollers 17, and the ultrasonic transducers 1 are not displaced with respect to the weld 12, which is essential for ultrasonic inspection of this weld 12. As the device moves on, the same obstacle (e.g. the transverse weld) is overcome by the ultrasonic transducers 1, owing to their being fixed on the flexible members 8 and owing to the gradual, rounded area of transition from the point of attachment of a transducer 1 to the flexible member 8, to the surface of the transducer 1 engaging the surface 4 of the article 2 (see FIG. 4).

Then the same obstacle is overcome by the trailing (in the direction of the travel) wheel 33 at the same side of the device as the previously mentioned leading wheel 33. The trailing rocker 11 with the common base 18 with the rollers 17 mounted thereon rocks, but the arcuate member 16 engaging these rollers 17 by its working surfaces 20 and 21 turns among the rollers 17, and the position of the ultrasonic transducers 1 with respect to the weld 12 remains unchanged, which is essential for reliable inspection by the transducers 1 of the weld 12 in their motion relative to this weld 12.

Similar events take place when obstacles are overcome by other magnetic wheels 33 of the motion mechanism 6 and other ultrasonic transducers 1 of the device illustrated in FIGS. 1-6.

When the ultrasonic transducers 1 detect a flaw, the respective spot on the surface of the weld 12 is marked, e.g. with ink, and simultaneously the flaw is registered.

With the control operation completed, a command sent by the transmitter 36 arrests the device. The pallet 67 (FIG. 15) is brought against the rear wheels 33 of the device, and the device rolls onto the pallet 67. The device is then deenergized, the casing 70 is put on, and the device is carried to another weld to be inspected.

In operations of inspecting articles 2 with horizontal surfaces 4, as well as either vertical welds 12 or annular welds 12 of horizontal pipelines, it is expedient to remove the two reduction gears 34 with their electric motors 35 from the rear (in the travel direction) rocker 11 of the device illustrated in FIGS. 1 to 6, and to fixedly secure the base 18 associated with this rocker 11, so that the rear rocker 11 would not be able to rock relative to this base 18.

Prior to an operation of inspecting an article 43 (FIGS. 7 and 8) of a non-ferromagnetic material, e.g. of aluminium, the device embodying the invention is set on the pallet 67 (FIG. 15) with the test specimen 69, of which the curvature of the surface 68 and the material are identical with those of the article 43. Then the make-ready operations described hereinabove in connection with the device illustrated in FIGS. 1 to 6 are performed.

Additionally, at the opposite side of the tray 67, there is performed the adjustment of the height of the platform 44 (FIG. 7) with the hinges 51, to enable the platform 44 to overcome eventual obstacles, e.g. the beads of welds.

Figure 9:
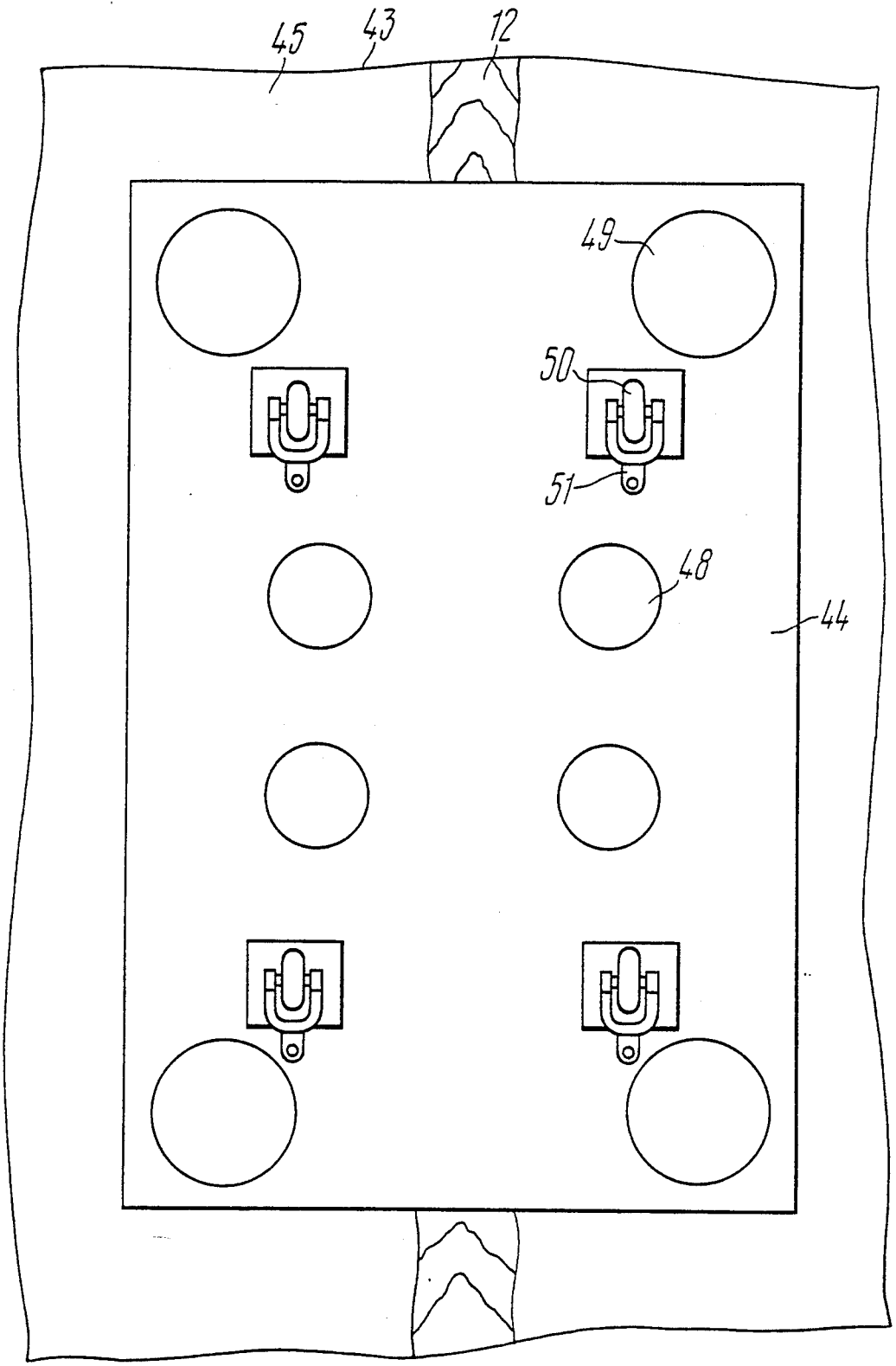
FIG. 9 is a view of the device of FIG. 7, taken along arrow line A.
Figure 10:
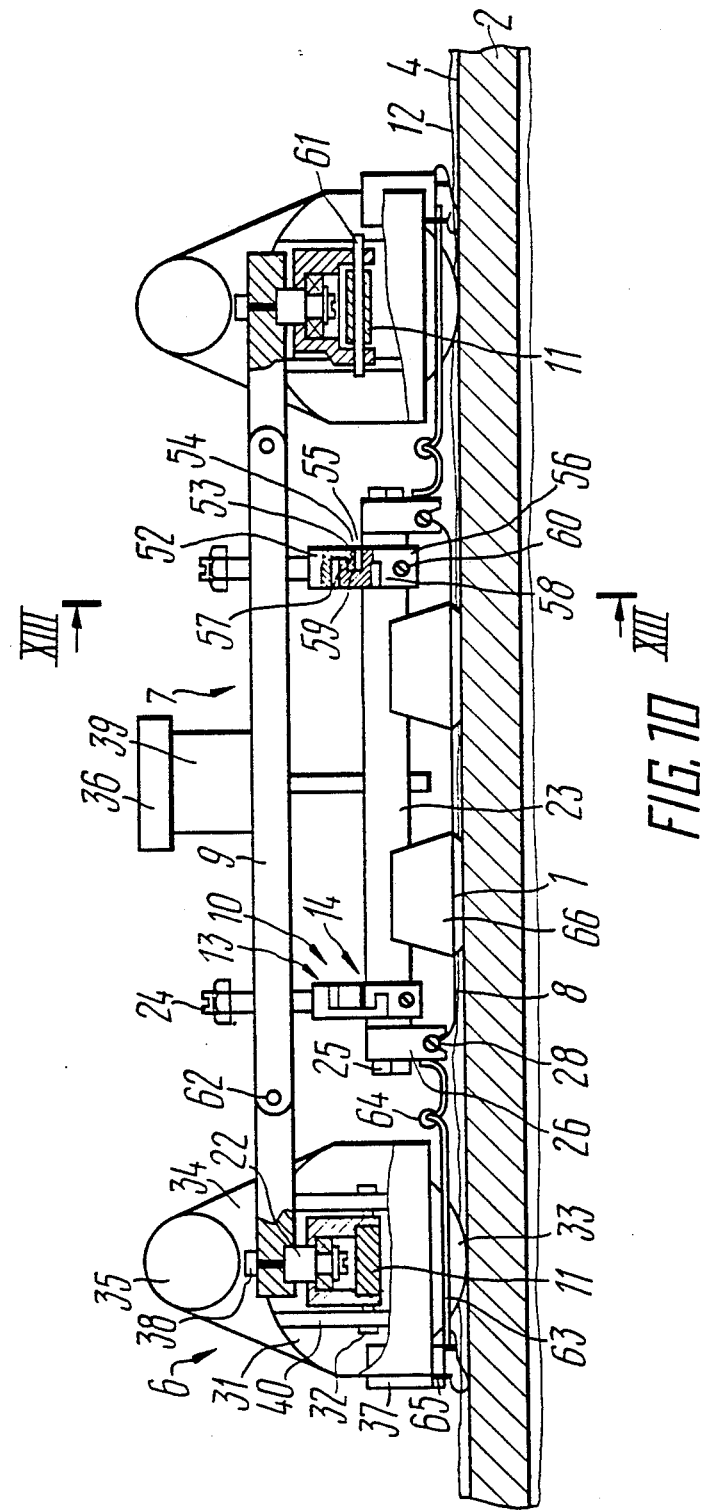
FIG. 10 is a partly broken away side view of yet another embodiment of a scanning device in accordance with the invention, with the inspected article shown in section.
Figure 11:
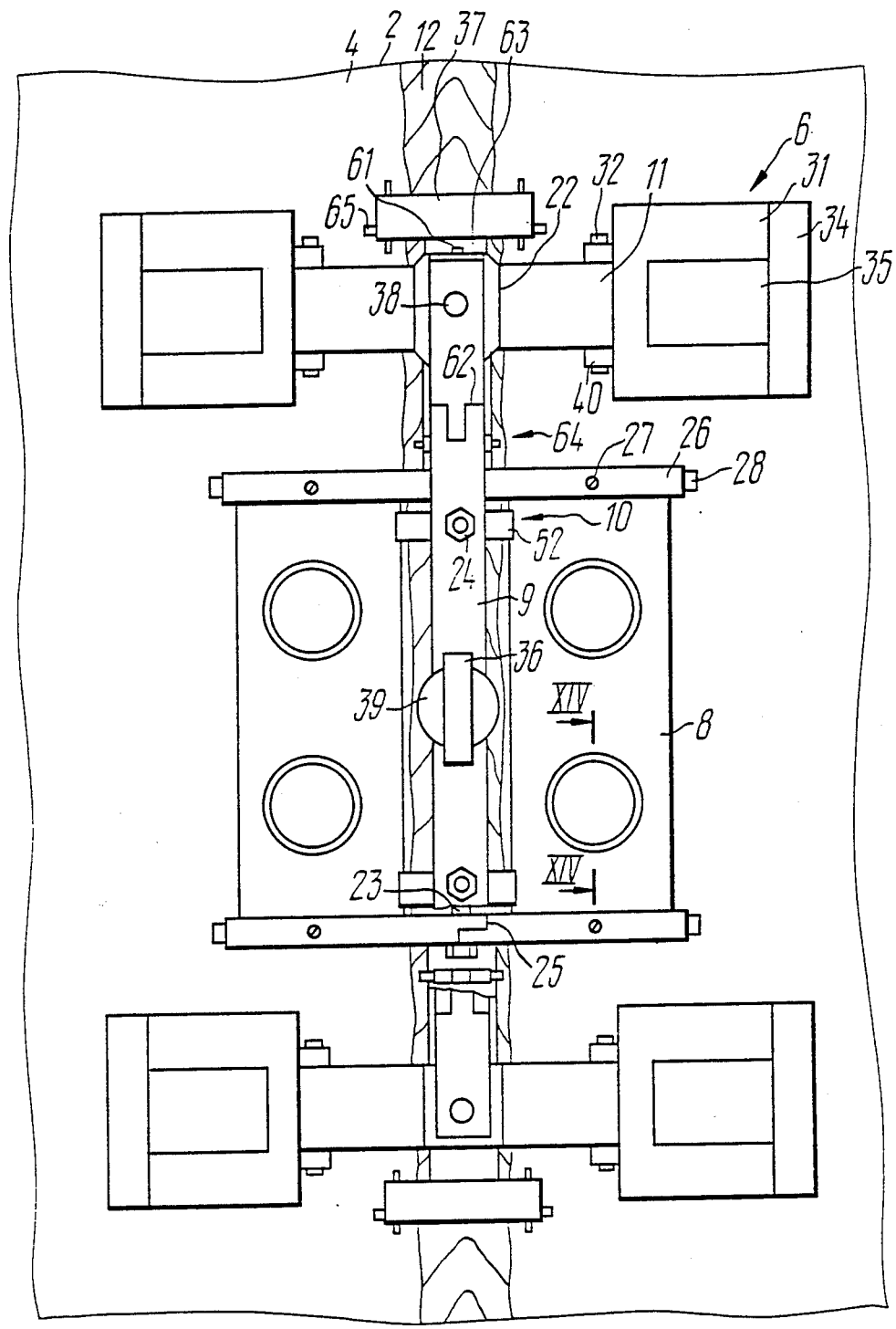
FIG. 11 is a partly broken away view in plan of the device of FIG. 10.
Figure 12:
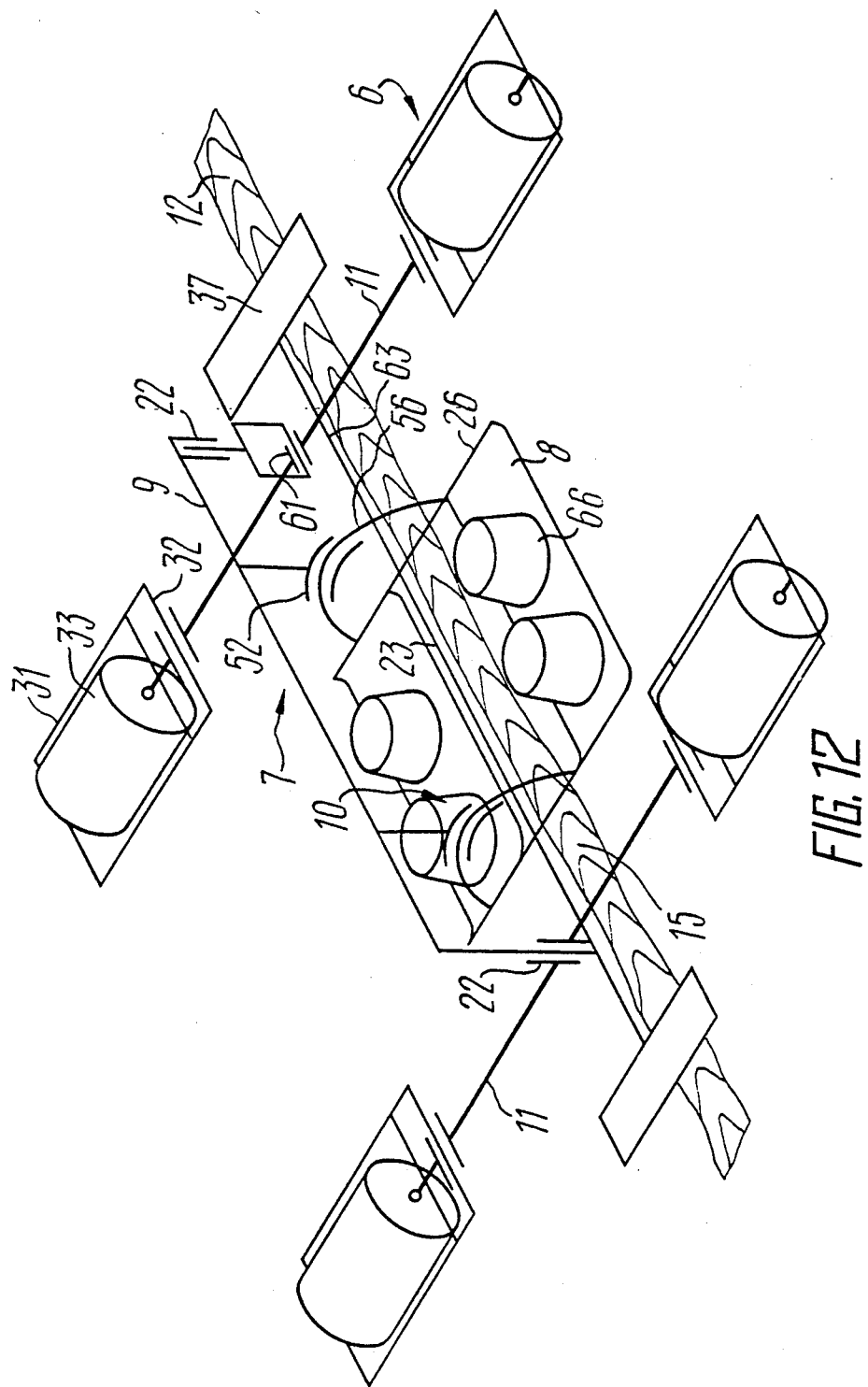
FIG. 12 is a mechanical diagram of the device of FIG. 10.
Figure 13:
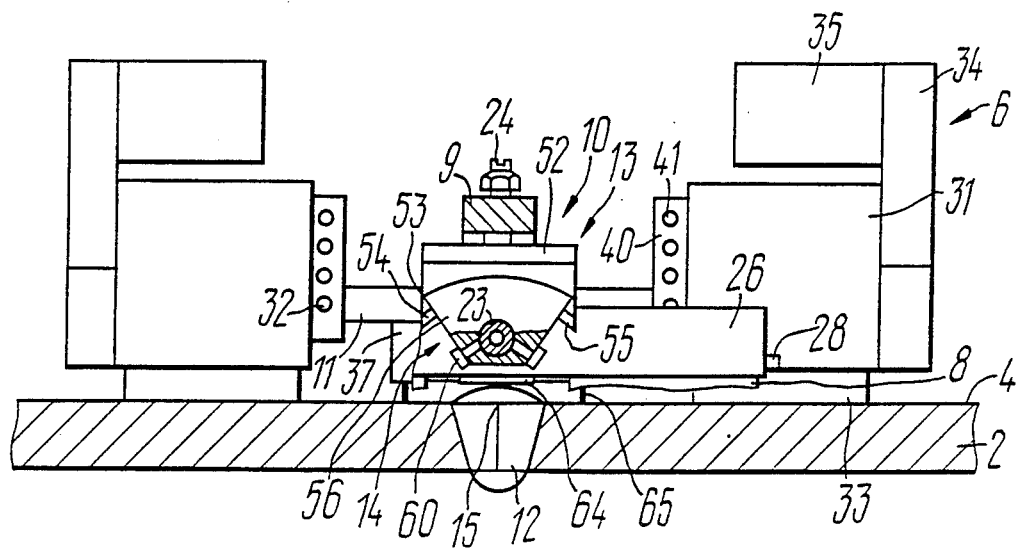
FIG. 13 is a sectional view taken on line XIII—XIII of FIG. 10.
Figure 14:
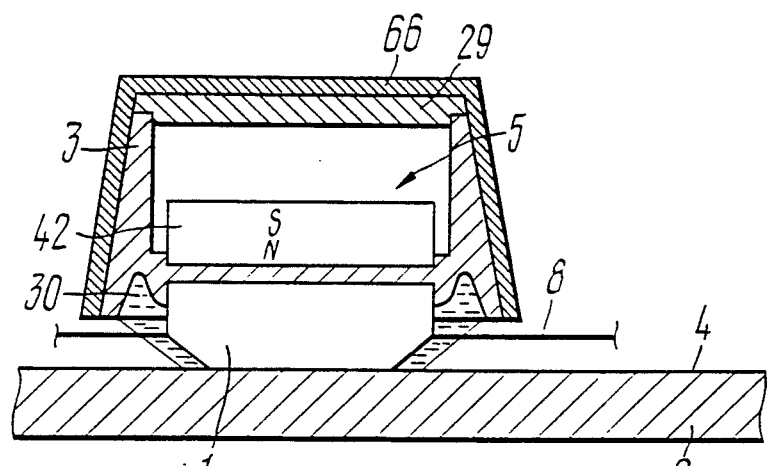
FIG. 14 shows an enlarged sectional view taken on line XIV—XIV of FIG. 11.

Thus adjusted, the entire device of FIGS. 7 to 9 is put onto the article 43 (FIG. 8) to be inspected, making sure that the respective axes of the pairs of the magnets 42 and 48 are aligned, and then the device is activated.

The ensuing operation is similar to the one described above.

Prior to quality control of an article 2 of a ferromagnetic material, the device of the embodiment illustrated in FIGS. 10 to 14 is set on the surface 68 (FIG. 15) of the pallet 67 with the test specimen 69. The curvature of the surface 68, the thickness and material of the test specimen 69 should be identical to those of the article 2 to be inspected. The beam 9 is indexed in the direction of the intended travel of the scanning device, indicated with arrows B (FIG. 11) and C.

The pivots 32 (FIGS. 10 and 13) are used to secure the respective ends of the rockers 11 in the lugs 40 (with the holes 41) of the housings 31 of the motion mechanism 6 at the required height, and the pivots 62 and screw-and-nut couples 24 are adjusted to set the respective self-aligning supports 10 at the height ensuring that the common rolling axis 15 belongs to the surface 68 (FIG. 15). The bar 23 (FIGS. 10 and 13) with the holders 26 of the flexible members 8, the sensors 37 for tracing the weld 12, the leaf springs 63 and pivots 64 are set above the surface 68 (FIG. 15) at the respective heights permitting the device to overcome obstacles that are tolerated on the article 2 (FIGS. 10 and 13) in compliance with the corresponding specifications, e.g. the beads of welds adjoining the weld 12 being inspected.

The holders 26 and springs 63 are fixed by operating the pivot 25, and the elements 28 for tensioning the flexible members 8 are operated to adjust the position of the ultrasonic transducers 1 with respect to the test specimen 69 (FIG. 15) so that they should sound out the entire inspected section of the article 2 (FIGS. 10 and 13), i.e. the entire volume of the weld 12 and its adjoining zones, whereafter the ends of the flexible members 8 jointly with the tensioning elements 28 are secured with the lock screws 27.

Then the operability of the transmitter 36, sensors 37 and 38, and flaw marker 39 is checked, and the activation of the limit switches 65 is adjusted.

A ferromagnetic fluid is poured into the internal cavities 30 (FIG. 14) of the respective housings 3 to maintain stable acoustic contact between the ultrasonic transducers 1 and the surface 68 (FIG. 15) of the test specimen 69, and the operability of all the ultrasonic transducers 1 is checked. The pallet 67 with the inspection-ready device illustrated in FIGS. 10 to 14 is brought against the article 2 to be inspected, and the device embodying the invention rolls onto the surface 4 of the article 2.

The motion of the device over the surface 4 of the article 2 under inspection is due to rotation of the magnetic wheels 33 maintained in reliable engagement with the surface 4, with the rotation being transmitted to the magnetic wheels 33 mounted on the output shafts of the respective reduction gears 34 from the output shafts of the electric motors 35 associated with these reduction gears 34. By varying selectively the speed of rotation of the individual electric motors 35, the rockers 11 (FIG. 12) are set at various angular attitudes with respect to the beam 9, owing to the existence of the pivots 22 and 61. By processing the signals sent by the sensors 37 tracing the weld 12, the angular position sensors 38, the transmitter 36 of the beginning and terminating of the control operation, the travelled path transmitter (not shown), the speeds of rotation of the individual magnetic wheels 33 are controlled so that the device should attain the required attitude in its travel over the surface 4 of the article 2 under inspection.

When the device encounters an obstacle of a height which is beyond the specified tolerances for the given article 2, (e.g. an abnormally high weld), the limit switch 65 mounted on the leading (in the travel direction) sensor 37 for tracing the weld 12 would send a signal to arrest the device.

If the ultrasonic transducers 1 become displaced in either direction away from the weld 12 being inspected, a signal sent by the corresponding sensor 37 would initiate the braking of the corresponding electric motor 35, so that one rocker 11 would turn about the pivot 22, and the other rocker 11 would turn about the pivot 61, and the device embodying the invention would return to the weld 12.

When horizontal welds are inspected on either vertical or inclined surfaces, the weight of the device makes the rear (in the travel direction) wheels 33 shift downwardly relative to the weld 12 being inspected. In this case the corresponding tracing sensor 37 also shifts, initiating a command sent to the appropriate electric motor 35 to bring down the speed of rotation of the respective magnetic wheel 33. This slowed-down rotation of the wheel 33 makes the rocker 11 of the rear (in the travel direction) wheels 33 to turn about the pivot 22, returning the device to the axis of the weld 12, in which way the disclosed device attains the required attitude for the quality control operation, and thus travels over the surface 4 of the article 2. The transmitter 36 sends a signal of the beginning of the quality control operation, and the ultrasonic transducers 1 are activated to sound out the entire inspected section of the article 2.

If a flaw is detected, the marker 39 is actuated to apply a mark onto the respective spot of the surface 4 of the article 2 under inspection, e.g. with ink. When the transmitter 36 sends a signal for the termination of the quality control operation, the device is arrested. The pallet 67 (FIG. 15) is brought against the device, and the device rolls onto the pallet 67.

In operation of the device illustrated in FIGS. 10 to 14, when its leading (in the travel direction) wheel encounters an obstacle within the tolerances specified for the given article 2 and rolls onto it by the outer edge of this wheel 33, the latter slants, turning on the pivot 32, without affecting the attitude of the beam 9 and trailing (in the travel direction) wheels 33.

If an obstacle within the specified tolerances lifts a leading wheel 33 bodily, the rocker 11 of this leading wheel 33 would turn, somewhat lifting its end of the beam 9 and the support 10 of the trailing wheels 33 which would not clear, however, the surface 4 of the article 2 under inspection, as their own rocker 11 would turn appropriately about the pivot 61. Meanwhile, the ultrasonic transducers 1 held by the magnets 42 against the surface 4 of the article 2 would not shift from their engagement with the surface 4, as the beam 9 with the guideway 52 would turn relative to the shell 56, and the flexible member 8 at the side of the trailing wheels 33 would become additionally tensioned, compensating for the slight lift of the bar 23 with the holders 26.

When the device rolls onto a weld, the limit switch 65 of the leading (in the travel direction) tracing sensor 37 would turn and send a signal to inactivate the sensor 37 for the time of the travel over the weld, preventing the sending of a false signal of deviation of the device from the predetermined travel direction. A signal from the limit switch 65 would also initiate the inactivation of the ultrasonic transducers 1 disposed at the same side of the inspected weld 12 for the time of the crossing of the transverse weld.

Other features of the operation of the device illustrated in FIGS. 10 to 14 are similar to the operation of the device illustrated in FIGS. 1 to 6.

The disclosed scanning device for ultrasonic quality control of articles provides for enhancing the reliability and credibility of the quality control operation, while having relatively small dimensions and weight and a simplified structure of the suspension assembly; moreover, it allows to broaden the range of inspected articles with different curvatures of their surfaces, made either of ferromagnetic materials or non-ferromagnetic materials, in various spatial attitudes of the device.

Furthermore, the fixed mounting of the ultrasonic transducers of the disclosed device on flexible members directly adjoining the surface of the inspected article, and the above described specific design of the suspension assembly provide for overcoming various obstacles on the surface of the inspected article, such as the beads of welds or splashes of metal left after the welding, irrespective of the curvature of the surface of the article. The permanent magnets of the hold-down means of the disclosed device provide for employing a ferromagnetic fluid for maintaining stable acoustic contact between the ultrasonic transducers of the device and the surface of the article under inspection, in diverse spatial attitudes of the device, at ambient temperatures from $-50°$ C. to $+50°$ C.

Thus, a prototype of a scanning device embodying the invention, used for inspecting annual welds of major pipelines of a 1420 mm diameter, with the wall thickness to 40 mm, under field conditions weighs less than 8 kg and is handled by one operator, and the time of quality control of one complete welded joint of a pipeline is less than 4 minutes.

INDUSTRIAL APPLICABILITY

The invention can be employed in various industries, more specifically, in general engineering, shipbuilding, nuclear power engineering, boiler manufacture, construction of gas and oil pipelines for ultrasonic quality control and inspection of welded joints and basic material of either ferromagnetic or nonferromagnetic articles being inspected with flat and curved surfaces, the device being capable of attaining various attitudes in space and of overcoming such obstacles as splashes of metal remaining after the welding, or else the beads of welds in cases of misalignment of the welded edges, while automatically tracing the axis of a weld or automatically carrying the ultrasonic transducers over a predetermined area.

We claim:

1. A scanning device for ultrasonic quality control of articles, comprising:
   a motion mechanism of said scanning device for moving said device along a direction of travel;
   ultrasonic transducers adapted to be positioned on an article under inspection;
   a suspension assembly for mounting said ultrasonic transducers on said motion mechanism, said assembly establishing an operative connection between ultrasonic transducers and said motion mechanism, said assembly including,
   flexible members positioned above the surface of said article under inspection along the direction of the travel of said device, preset with said motion mechanism,
   said flexible members having said ultrasonic transducers fixedly mounted thereon,
   a beam having a first end and a second end, extending above said flexible members along said direction of the travel of said device, mechanically connected with said flexible members,
   at least two self-aligning supports having a common rolling axis extending in direct proximity to said surface of said article under inspection,
   each said self-aligning support including,
   a first part carried by said beam, and
   a second part arranged with respect to said first part so that relative displacement of said two parts takes place about said rolling axis common to said self-aligning supports, and
   two rockers operatively connected with said beam and said motion mechanism;
   means for holding said ultrasonic transducers against said surface of said article under inspection.

2. A scanning device as set forth in claim 1, wherein:
   said first part of each said self-aligning support includes:
   an arcuate member having working surfaces and defining a longitudinal central axis which is said common rolling axis of said at least two self-aligning support, mounted on said first or second end of said beam, and
   said second part of each said self-aligning support includes:
   at least three rollers engaging said working surfaces of said arcuate member, and
   a common base carrying said rollers establishing operative connection between one of said rockers and said beam through said arcuate member and said base.

3. A scanning device as set forth in claim 1, wherein:
   said first part of each said self-aligning support includes:
   a guideway secured to said beam and having a first cylindrical working surface having a first longitudinal axis, a second cylindrical working surface having a second longitudinal axis, and a first planar working surface interconnecting said cylindrical working surfaces;

said second part of each said self-aligning supports includes:
a shell having a third cylindrical working surface having a third longitudinal axis, congruent with said first cylindrical surface and engaged thereby, a fourth cylindrical working surface having a fourth longitudinal axis, congruent with said second cylindrical working surface and engaged thereby, and a second planar surface interconnecting said third cylindrical surface and said fourth cylindrical surface, and engaging said first planar working surface, all said longitudinal axes coinciding and defining said common rolling axis for said self-aligning supports.

4. A scanning device as set forth in claim 1, adapted for quality control of articles of ferromagnetic materials, wherein said means for holding said ultrasonic transducers against said surface of said article under inspection includes:
permanent magnets having respective S poles and N poles, directly overlying each of said ultrasonic transducers fixedly mounted on said flexible members.

5. A scanning device as set forth in claim 1, adapted for quality control of articles of non-ferromagnetic materials, wherein said means for holding said ultrasonic transducers against said surface of said article under inspection includes:
first permanent magnets having respective S poles and N poles, directly overlying each of said ultrasonic transducers fixedly mounted on said flexible members;
a platform positioned adjacent to the surface of said article under inspection at the side opposite to said surface of said article at which quality control is performed, adapted for automatically following the direction of the travel of said scanning device, and
second permanent magnets having respective S poles and N poles, mounted on said platform with their either S poles or N poles facing the opposite N poles or S poles of said respective first permanent magnets, symmetrically therewith.

6. A scanning device as set forth in claim 2, adapted for quality control of articles of ferromagnetic materials, wherein said means for holding said ultrasonic transducers against said surface of said article under inspection includes:
permanent magnets having respective S poles and N poles, directly overlying each of said ultrasonic transducers fixedly mounted on said flexible members.

7. A scanning device as set forth in claim 2, adapted for quality control of articles of non-ferromagnetic materials, wherein said means for holding said ultrasonic transducers against said surface of said article under inspection includes:
first permanent magnets having respective S poles and N poles, directly overlying each of said ultrasonic transducers fixedly mounted on said flexible members;
a platform positioned adjacent to the surface of said article under inspection at the side opposite to said surface of said article at which quality control is performed, adapted for automatically following the direction of the travel of said scanning device, and
second permanent magnets having respective S poles and N poles, mounted on said platform with their either S poles or N poles facing the opposite N poles or S poles of said respective first permanent magnets, symmetrically therewith.

8. A scanning device as set forth in claim 3, adapted for quality control of articles of ferromagnetic materials, wherein said means for holding said ultrasonic transducers against said surface of said article under inspection includes:
permanent magnets having respective S poles and N poles, directly overlying each of said ultrasonic transducers fixedly mounted on said flexible members.

9. A scanning device as set forth in claim 3, adapted for quality control of articles of non-ferromagnetic materials, wherein said means for holding said ultrasonic transducers against said surface of said article under inspection includes:
first permanent magnets having respective S poles and N poles, directly overlying each of said ultrasonic transducers fixedly mounted on said flexible members;
a platform positioned adjacent to the surface of said article under inspection at the side opposite to said surface of said article at which quality control is performed, adapted for automatically following the direction of the travel of said scanning device, and
second permanent magnets having respective S poles and N poles, mounted on said platform with their either S poles or N poles facing the opposite N poles or S poles of said respective permanent magnets, symmetrically therewith.

10. A scanning device for ultrasonic quality control of articles, comprising:
a motion mechanism of said scanning device for moving said device along a direction of travel;
ultrasonic transducers adapted to be positioned on an article under inspection;
a suspension assembly for mounting said ultrasonic transducers on said motion mechanism, said assembly establishing an operative connection between said ultrasonic transducers and said motion mechanism, said assembly including
flexible members positioned above the surface of said article under inspection along the direction of the travel of said device, preset with said motion mechanism,
said flexible members having said ultrasonic transducers fixedly mounted thereon,
a beam having a first end and a second end, extending above said flexible members along said direction of the travel of said device, mechanically connected with said flexible members,
two rockers operatively connected with said beam and said motion mechanism, and
at least two self-aligning supports having a common rolling axis extending in direct proximity to said surface of said article under inspection,
each said self-aligning support including
a first part having an arcuate member having working surfaces and defining a central longitudinal axis which is said common rolling axis of said at least two self-aligning support, mounted on said first or second end of said beam, and
a second part arranged with respect to said first part so that relative displacement of said two parts takes place about said rolling axis common to said self-aligning supports, said second part including
- at least three rollers engaging said working surfaces of said arcuate member, and
- a common base carrying said rollers establishing operative connection between one of said rockers and said beam through said arcuate member and said base;

means for holding said ultrasonic transducers against said surface of said article under inspection, including permanent magnets having respective S poles and N poles, directly overlying each of said ultrasonic transducers fixedly mounted on said flexible members, for performing quality control of articles of ferromagnetic materials.

11. A scanning device for ultrasonic quality control of articles, comprising:
- a motion mechanism of said scanning device for moving said device along a direction of travel;
- ultrasonic transducers adapted to be positioned on an article under inspection;
- a suspension assembly for mounting said ultrasonic transducers on said motion mechanism, said assembly establishing an operative connection between said ultrasonic transducers and said motion mechanism, including,
- flexible members positioned above the surface of said article under inspection along the direction of the travel of said device, preset with said motion mechanism,
- said flexible members having said ultrasonic transducers fixedly mounted thereon,
- a beam having a first end and a second end, extending above said flexible members along said direction of the travel of said device, mechanically connected with said flexible members,
- at least two self-aligning supports having a common rolling axis extending in direct proximity to said surface of said article under inspection,
- each said self-aligning support including,
  - a first part having a guideway secured to said beam and having a first cylindrical working surface having a first longitudinal axis, a second cylindrical working surface having a second longitudinal axis, and a first planar working surface interconnecting said cylindrical working surfaces,
  - a second part arranged with respect to said first part so that relative displacement of said two parts takes place about said rolling axis common to said self-aligning supports,
  - said second part including,
  - a shell having a third cylindrical working surface having a third longitudinal axis, congruent with said first cylindrical surface and engaged thereby, a fourth cylindrical working surface having a fourth longitudinal axis, congruent with said second cylindrical surface and engaged thereby, and a second planar surface interconnecting said third cylindrical surface and said fourth cylindrical surface, and engaging said first planar working surface, all said longitudinal axes coinciding and defining said common rolling axis for said self-aligning supports, and
- two rockers operatively connected with said beam and said motion mechanism; and means for holding said ultrasonic transducers against said surface of said article under inspection, including, first permanent magnets having respective S poles and N poles, directly overlying each of said ultrasonic transducers fixedly mounted on said flexible members, for performing quality control of articles of ferromagnetic materials, a platform positioned adjacent to the surface of said article under inspection at the side opposite to said surface of said article at which quality control is performed, adapted for automatically following the direction of the travel of said scanning device, and second permanent magnets having respective S poles and N poles, mounted on said platform with their either S poles or N poles facing the opposite N poles or S poles of said respective first permanent magnets, symmetrically therewith, for performing quality control of articles of non-ferromagnetic materials together with said first permanent magnets.

12. A scanning device for ultrasonic quality control of articles, comprising:
- a motion mechanism of said scanning device for moving said device along a direction of travel;
- ultrasonic transducers adapted to be positioned on an article under inspection;
- a suspension assembly for mounting said ultrasonic transducers on said motion mechanism, said assembly establishing an operative connection between said ultrasonic transducers and said motion mechanism, said assembly including
- flexible members positioned above the surface of said article under inspection along the direction of the travel of said device, preset with said motion mechanism,
- said flexible members having said ultrasonic transducers fixedly mounted thereon,
- a beam having a first end and a second end, extending above said flexible members along said direction of the travel of said device, mechanically connected with said flexible members,
- two rockers operatively connected with said beam and said motion mechanism, and
- at least two self-aligning supports having a common rolling axis extending in direct proximity to said surface of said article under inspection,
- each said self-aligning support including
  - a first part having an arcuate member having working surfaces and defining a central longitudinal axis which is said common rolling axis of said at least two self-aligning supports, mounted on said first or second end of said beam, and
  - a second part arranged with respect to said first part so that relative displacement of said two parts takes place about said rolling axis common to said self-aligning supports,
  - said second part including
    - at least three rollers engaging said working surfaces of said arcuate member, and
    - a common base carrying said rollers establishing operative connection between one of said rockers and said beam through said arcuate member and said base; and means for holding said ultrasonic transducers against said surface of said article under inspection including first permanent magnets having respective S poles and N poles, directly overlying each of said ultrasonic transducers, fixedly mounted on said flexible members, for performing quality control of articles of ferromagnetic materials, a platform positioned adjacent to the surface of said article under inspection at the side opposite to said surface of said article at which quality control is performed, adapted for automatically following the direction of the travel of said scanning device, and second permanent magnets having respective S poles and N poles, mounted on said platform with their either S poles or N poles facing the opposite N poles or S poles of said respective first permanent magnets, symmetrically therewith, for performing quality control of articles of non-ferromagnetic materials together with said first permanent magnets.

* * * * *